(12) United States Patent
Orszulak et al.

(10) Patent No.: US 7,927,328 B2
(45) Date of Patent: Apr. 19, 2011

(54) SYSTEM AND METHOD FOR CLOSED LOOP MONITORING OF MONOPOLAR ELECTROSURGICAL APPARATUS

(75) Inventors: James H. Orszulak, Nederland, CO (US); Robert H. Wham, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1121 days.

(21) Appl. No.: 11/657,174

(22) Filed: Jan. 24, 2007

(65) Prior Publication Data

US 2007/0173806 A1 Jul. 26, 2007

Related U.S. Application Data

(60) Provisional application No. 60/761,440, filed on Jan. 24, 2006.

(51) Int. Cl.
*A61B 18/18* (2006.01)
(52) U.S. Cl. .............................. 606/34; 606/38
(58) Field of Classification Search .............. 606/32–35, 606/37–40
See application file for complete search history.

(56) References Cited

U.S. PATENT DOCUMENTS

| | | | |
|---|---|---|---|
| 1,787,709 A | 1/1931 | Wappler | |
| 1,813,902 A | 7/1931 | Bovie | |
| 1,841,968 A | 1/1932 | Lowry | |
| 1,863,118 A | 6/1932 | Liebel | |
| 1,945,867 A | 2/1934 | Rawls | |
| 2,827,056 A | 3/1958 | Degelman | |
| 2,849,611 A | 8/1958 | Adams | |
| 3,058,470 A | 10/1962 | Seeliger et al. | |
| 3,089,496 A | 5/1963 | Degelman | |
| 3,154,365 A | 10/1964 | Crimmins | |
| 3,163,165 A | 12/1964 | Isikawa | |
| 3,252,052 A | 5/1966 | Nash | |
| 3,391,351 A | 7/1968 | Trent | |
| 3,413,480 A | 11/1968 | Biard et al. | |
| 3,436,563 A | 4/1969 | Regitz | |
| 3,439,253 A | 4/1969 | Piteo | |
| 3,439,680 A | 4/1969 | Thomas, Jr. | |
| 3,461,874 A | 8/1969 | Martinez | |

(Continued)

FOREIGN PATENT DOCUMENTS

DE 179607 3/1905

(Continued)

OTHER PUBLICATIONS

International Search Report EP 07008207.8; dated Sep. 5, 2007.

(Continued)

*Primary Examiner* — Linda C Dvorak
*Assistant Examiner* — Amanda Scott (57) ABSTRACT

An electrosurgical system is disclosed comprising a generator configured to electrosurgical coagulation waveforms. The generator includes a closed loop control system for controlling the electrosurgical coagulation waveforms. The closed loop control system includes a sensor configured to sense a tissue property and/or an energy property and to transmit the tissue property and/or the energy property as one or more sensor signals having an amplitude. The control system also includes a gain controller configured to process the at least one sensor signal to reduce the amplitude of the sensor signals and to obtain a signal to noise ratio of the at sensor signals within a predetermine range. A microprocessor coupled to the generator and is configured to adjust the electrosurgical coagulation waveforms as a function of the sensor signals.

18 Claims, 2 Drawing Sheets

U.S. PATENT DOCUMENTS

| | | |
|---|---|---|
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |

| | | | | | |
|---|---|---|---|---|---|
| 5,067,953 A | 11/1991 | Feucht | 5,438,302 A | 8/1995 | Goble |
| 5,075,839 A | 12/1991 | Fisher et al. | 5,443,463 A | 8/1995 | Stern et al. |
| 5,087,257 A | 2/1992 | Farin | 5,445,635 A | 8/1995 | Denen |
| 5,099,840 A | 3/1992 | Goble et al. | 5,451,224 A | 9/1995 | Goble et al. |
| 5,103,804 A | 4/1992 | Abele et al. | 5,452,725 A | 9/1995 | Martenson |
| 5,108,389 A | 4/1992 | Cosmescu | 5,454,809 A | 10/1995 | Janssen |
| 5,108,391 A | 4/1992 | Flachenecker | 5,458,597 A | 10/1995 | Edwards et al. |
| 5,119,284 A | 6/1992 | Fisher et al. | 5,462,521 A | 10/1995 | Brucker et al. |
| 5,122,137 A | 6/1992 | Lennox | 5,472,441 A | 12/1995 | Edwards et al. |
| 5,133,711 A | 7/1992 | Hagen | 5,472,443 A | 12/1995 | Cordis et al. |
| 5,151,102 A | 9/1992 | Kamiyama et al. | 5,474,464 A | 12/1995 | Drewnicki |
| 5,152,762 A | 10/1992 | McElhenney | 5,480,399 A | 1/1996 | Hebborn |
| 5,157,603 A | 10/1992 | Scheller et al. | 5,483,952 A | 1/1996 | Aranyi |
| 5,160,334 A | 11/1992 | Billings et al. | 5,496,312 A | 3/1996 | Klicek |
| 5,161,893 A | 11/1992 | Shigezawa et al. | 5,496,313 A | 3/1996 | Gentelia et al. |
| 5,167,658 A | 12/1992 | Ensslin | 5,496,314 A | 3/1996 | Eggers |
| 5,167,659 A | 12/1992 | Ohtomo et al. | 5,500,012 A | 3/1996 | Brucker et al. |
| 5,190,517 A | 3/1993 | Zieve et al. | 5,500,616 A | 3/1996 | Ochi |
| 5,196,008 A | 3/1993 | Kuenecke | 5,511,993 A | 4/1996 | Yamada et al. |
| 5,196,009 A | 3/1993 | Kirwan, Jr. | 5,514,129 A | 5/1996 | Smith |
| 5,201,900 A | 4/1993 | Nardella | 5,520,684 A | 5/1996 | Imran |
| 5,207,691 A | 5/1993 | Nardella | 5,531,774 A | 7/1996 | Schulman et al. |
| 5,230,623 A | 7/1993 | Guthrie et al. | 5,534,018 A | 7/1996 | Wahlstrand et al. |
| 5,233,515 A | 8/1993 | Cosman | 5,536,267 A | 7/1996 | Edwards et al. |
| 5,234,427 A | 8/1993 | Ohtomo et al. | 5,540,677 A | 7/1996 | Sinofsky |
| 5,249,121 A | 9/1993 | Baum et al. | 5,540,681 A | 7/1996 | Strul et al. |
| 5,249,585 A | 10/1993 | Turner et al. | 5,540,682 A | 7/1996 | Gardner et al. |
| 5,254,117 A | 10/1993 | Rigby et al. | 5,540,683 A | 7/1996 | Ichikawa |
| RE34,432 E | 11/1993 | Bertrand | 5,540,684 A | 7/1996 | Hassler, Jr. |
| 5,267,994 A | 12/1993 | Gentelia et al. | 5,541,376 A | 7/1996 | Ladtkow et al. |
| 5,267,997 A | 12/1993 | Farin | 5,545,161 A | 8/1996 | Imran |
| 5,281,213 A | 1/1994 | Milder et al. | 5,556,396 A | 9/1996 | Cohen et al. |
| 5,282,840 A | 2/1994 | Hudrlik | 5,558,671 A | 9/1996 | Yates |
| 5,290,283 A | 3/1994 | Suda | 5,562,720 A | 10/1996 | Stern et al. |
| 5,295,857 A | 3/1994 | Toly | 5,569,242 A | 10/1996 | Lax et al. |
| 5,300,068 A | 4/1994 | Rosar et al. | 5,571,147 A | 11/1996 | Sluijter et al. |
| 5,300,070 A | 4/1994 | Gentelia | 5,573,533 A | 11/1996 | Strul |
| 5,304,917 A | 4/1994 | Somerville | 5,584,830 A | 12/1996 | Ladd et al. |
| 5,318,563 A | 6/1994 | Malis et al. | 5,588,432 A | 12/1996 | Crowley |
| 5,323,778 A | 6/1994 | Kandarpa et al. | 5,596,466 A | 1/1997 | Ochi |
| 5,324,283 A | 6/1994 | Heckele | 5,599,344 A | 2/1997 | Paterson |
| 5,330,518 A | 7/1994 | Neilson et al. | 5,599,345 A | 2/1997 | Edwards et al. |
| 5,334,183 A | 8/1994 | Wuchinich | 5,599,348 A | 2/1997 | Gentelia et al. |
| 5,334,193 A | 8/1994 | Nardella | 5,605,150 A | 2/1997 | Radons et al. |
| 5,341,807 A | 8/1994 | Nardella | 5,609,560 A | 3/1997 | Ichikawa et al. |
| 5,342,356 A | 8/1994 | Ellman | 5,613,966 A | 3/1997 | Makower et al. |
| 5,342,357 A | 8/1994 | Nardella | 5,620,481 A | 4/1997 | Desai et al. |
| 5,342,409 A | 8/1994 | Mullett | 5,626,575 A | 5/1997 | Crenner |
| 5,346,406 A | 9/1994 | Hoffman et al. | 5,628,745 A | 5/1997 | Bek |
| 5,346,491 A | 9/1994 | Oertli | 5,628,771 A | 5/1997 | Mizukawa et al. |
| 5,348,554 A | 9/1994 | Imran et al. | 5,643,330 A | 7/1997 | Holsheimer et al. |
| 5,370,645 A * | 12/1994 | Klicek et al. .................. 606/35 | 5,647,869 A | 7/1997 | Goble et al. |
| 5,370,672 A | 12/1994 | Fowler et al. | 5,647,871 A | 7/1997 | Levine et al. |
| 5,370,675 A | 12/1994 | Edwards et al. | 5,651,780 A | 7/1997 | Jackson et al. |
| 5,372,596 A | 12/1994 | Klicek et al. | 5,658,322 A | 8/1997 | Fleming |
| 5,383,874 A | 1/1995 | Jackson | 5,660,567 A | 8/1997 | Nierlich et al. |
| 5,383,876 A | 1/1995 | Nardella | 5,664,953 A | 9/1997 | Reylek |
| 5,383,917 A | 1/1995 | Desai et al. | 5,674,217 A | 10/1997 | Wahlstrom et al. |
| 5,385,148 A | 1/1995 | Lesh et al. | 5,678,568 A | 10/1997 | Uchikubo et al. |
| 5,400,267 A | 3/1995 | Denen et al. | 5,681,307 A | 10/1997 | McMahan |
| 5,403,311 A | 4/1995 | Abele et al. | 5,685,840 A | 11/1997 | Schechter et al. |
| 5,403,312 A | 4/1995 | Yates et al. | 5,688,267 A | 11/1997 | Panescu et al. |
| 5,409,000 A | 4/1995 | Imran | 5,693,042 A | 12/1997 | Boiarski et al. |
| 5,409,485 A | 4/1995 | Suda | 5,693,078 A | 12/1997 | Desai et al. |
| 5,413,573 A | 5/1995 | Koivukangas | 5,694,304 A | 12/1997 | Telefus et al. |
| 5,414,238 A | 5/1995 | Steigerwald et al. | 5,695,494 A | 12/1997 | Becker |
| 5,417,719 A | 5/1995 | Hull et al. | 5,696,441 A | 12/1997 | Mak et al. |
| 5,422,567 A | 6/1995 | Matsunaga | 5,697,925 A | 12/1997 | Taylor |
| 5,422,926 A | 6/1995 | Smith et al. | 5,697,927 A | 12/1997 | Imran et al. |
| 5,423,808 A | 6/1995 | Edwards et al. | 5,702,386 A | 12/1997 | Stern et al. |
| 5,423,809 A | 6/1995 | Klicek | 5,702,429 A | 12/1997 | King |
| 5,423,810 A | 6/1995 | Goble et al. | 5,707,369 A | 1/1998 | Vaitekunas et al. |
| 5,423,811 A | 6/1995 | Imran et al. | 5,712,772 A | 1/1998 | Telefus et al. |
| 5,425,704 A | 6/1995 | Sakurai et al. | 5,713,896 A | 2/1998 | Nardella |
| 5,429,596 A | 7/1995 | Arias et al. | 5,718,246 A | 2/1998 | Vona |
| 5,430,434 A | 7/1995 | Lederer et al. | 5,720,742 A | 2/1998 | Zacharias |
| 5,432,459 A | 7/1995 | Thompson | 5,720,744 A | 2/1998 | Eggleston et al. |
| 5,433,739 A | 7/1995 | Sluijter et al. | 5,722,975 A | 3/1998 | Edwards et al. |
| 5,436,566 A | 7/1995 | Thompson | 5,729,448 A | 3/1998 | Haynie et al. |

| | | | | | | |
|---|---|---|---|---|---|---|
| 5,733,281 A | 3/1998 | Nardella | | 6,063,075 A | 5/2000 | Mihori |
| 5,735,846 A | 4/1998 | Panescu et al. | | 6,063,078 A | 5/2000 | Wittkampf |
| 5,738,683 A | 4/1998 | Osypka | | 6,066,137 A | 5/2000 | Greep |
| 5,743,900 A | 4/1998 | Hara | | 6,068,627 A | 5/2000 | Orszulak et al. |
| 5,743,903 A | 4/1998 | Stern et al. | | 6,074,089 A | 6/2000 | Hollander et al. |
| 5,749,869 A | 5/1998 | Lindenmeier et al. | | 6,074,386 A | 6/2000 | Goble et al. |
| 5,749,871 A | 5/1998 | Hood et al. | | 6,074,388 A | 6/2000 | Tockweiler et al. |
| 5,755,715 A | 5/1998 | Stern | | 6,080,149 A | 6/2000 | Huang et al. |
| 5,766,153 A | 6/1998 | Eggers et al. | | 6,088,614 A | 7/2000 | Swanson |
| 5,766,165 A | 6/1998 | Gentelia et al. | | 6,093,186 A | 7/2000 | Goble |
| 5,769,847 A | 6/1998 | Panescu | | 6,102,497 A | 8/2000 | Ehr et al. |
| 5,772,659 A | 6/1998 | Becker et al. | | 6,102,907 A | 8/2000 | Smethers et al. |
| 5,788,688 A | 8/1998 | Bauer et al. | | 6,113,591 A | 9/2000 | Whayne et al. |
| 5,792,138 A | 8/1998 | Shipp | | 6,113,592 A | 9/2000 | Taylor |
| 5,797,902 A | 8/1998 | Netherly | | 6,113,593 A | 9/2000 | Tu et al. |
| 5,807,253 A | 9/1998 | Dumoulin et al. | | 6,113,596 A | 9/2000 | Hooven |
| 5,810,804 A | 9/1998 | Gough et al. | | 6,123,701 A | 9/2000 | Nezhat |
| 5,814,092 A | 9/1998 | King | | 6,123,702 A | 9/2000 | Swanson et al. |
| 5,817,091 A | 10/1998 | Nardella et al. | | 6,132,429 A | 10/2000 | Baker |
| 5,817,093 A | 10/1998 | Williamson, IV et al. | | 6,142,992 A | 11/2000 | Cheng et al. |
| 5,820,568 A | 10/1998 | Willis | | 6,155,975 A | 12/2000 | Urich et al. |
| 5,827,271 A | 10/1998 | Bussey et al. | | 6,162,184 A | 12/2000 | Swanson et al. |
| 5,830,212 A | 11/1998 | Cartmell | | 6,162,217 A | 12/2000 | Kannenberg et al. |
| 5,836,909 A | 11/1998 | Cosmescu | | 6,165,169 A | 12/2000 | Panescu et al. |
| 5,836,943 A | 11/1998 | Miller, III | | 6,171,304 B1 | 1/2001 | Netherly et al. |
| 5,836,990 A | 11/1998 | Li | | 6,183,468 B1 | 2/2001 | Swanson et al. |
| 5,843,019 A | 12/1998 | Eggers et al. | | 6,186,147 B1 | 2/2001 | Cobb |
| 5,843,075 A | 12/1998 | Taylor | | 6,188,211 B1 | 2/2001 | Rincon-Mora et al. |
| 5,846,236 A | 12/1998 | Lindenmeier et al. | | 6,193,713 B1 | 2/2001 | Geistert et al. |
| 5,849,010 A | 12/1998 | Wurzer et al. | | 6,197,023 B1 | 3/2001 | Muntermann |
| 5,853,409 A | 12/1998 | Swanson et al. | | 6,203,541 B1 | 3/2001 | Keppel |
| 5,860,832 A | 1/1999 | Wayt et al. | | 6,210,403 B1 | 4/2001 | Klicek |
| 5,865,788 A | 2/1999 | Edwards et al. | | 6,216,704 B1 | 4/2001 | Ingle et al. |
| 5,868,737 A | 2/1999 | Taylor et al. | | 6,222,356 B1 | 4/2001 | Taghizadeh-Kaschani |
| 5,868,739 A | 2/1999 | Lindenmeier et al. | | 6,228,078 B1 | 5/2001 | Eggers et al. |
| 5,868,740 A | 2/1999 | LeVeen et al. | | 6,228,080 B1 | 5/2001 | Gines |
| 5,871,481 A | 2/1999 | Kannenberg et al. | | 6,228,081 B1 | 5/2001 | Goble |
| 5,891,142 A | 4/1999 | Eggers et al. | | 6,231,569 B1 | 5/2001 | Bek |
| 5,897,552 A | 4/1999 | Edwards et al. | | 6,232,556 B1 | 5/2001 | Daugherty et al. |
| 5,906,614 A | 5/1999 | Stern et al. | | 6,235,020 B1 | 5/2001 | Cheng et al. |
| 5,908,444 A | 6/1999 | Azure | | 6,235,022 B1 | 5/2001 | Hallock et al. |
| 5,913,882 A | 6/1999 | King | | 6,237,604 B1 | 5/2001 | Burnside et al. |
| 5,921,982 A | 7/1999 | Lesh et al. | | 6,238,387 B1 | 5/2001 | Miller, III |
| 5,925,070 A | 7/1999 | King et al. | | 6,238,388 B1 | 5/2001 | Ellman |
| 5,931,836 A | 8/1999 | Hatta et al. | | 6,241,723 B1 | 6/2001 | Heim et al. |
| 5,938,690 A | 8/1999 | Law et al. | | 6,241,725 B1 | 6/2001 | Cosman |
| 5,944,553 A | 8/1999 | Yasui et al. | | 6,243,654 B1 | 6/2001 | Johnson et al. |
| 5,948,007 A | 9/1999 | Starkenbaum et al. | | 6,245,061 B1 | 6/2001 | Panescu et al. |
| 5,951,545 A | 9/1999 | Schilling | | 6,245,063 B1 | 6/2001 | Uphoff |
| 5,951,546 A | 9/1999 | Lorentzen | | 6,245,065 B1 | 6/2001 | Panescu |
| 5,954,686 A | 9/1999 | Garito et al. | | 6,246,912 B1 | 6/2001 | Sluijter et al. |
| 5,954,717 A | 9/1999 | Behl et al. | | 6,251,106 B1 | 6/2001 | Becker et al. |
| 5,954,719 A | 9/1999 | Chen et al. | | 6,254,422 B1 | 7/2001 | Feye-Hohmann |
| 5,957,961 A | 9/1999 | Maguire et al. | | 6,258,085 B1 | 7/2001 | Eggleston |
| 5,959,253 A | 9/1999 | Shinchi | | 6,261,285 B1 | 7/2001 | Novak |
| 5,961,344 A | 10/1999 | Rosales et al. | | 6,261,286 B1 | 7/2001 | Goble et al. |
| 5,964,746 A | 10/1999 | McCary | | 6,267,760 B1 | 7/2001 | Swanson |
| 5,971,980 A | 10/1999 | Sherman | | 6,273,886 B1 | 8/2001 | Edwards |
| 5,971,981 A | 10/1999 | Hill et al. | | 6,275,786 B1 | 8/2001 | Daners |
| 5,976,128 A | 11/1999 | Schilling et al. | | 6,293,941 B1 | 9/2001 | Strul |
| 5,983,141 A | 11/1999 | Sluijter et al. | | 6,293,942 B1 | 9/2001 | Goble et al. |
| 6,007,532 A | 12/1999 | Netherly | | 6,293,943 B1 | 9/2001 | Panescu et al. |
| 6,010,499 A | 1/2000 | Cobb | | 6,296,636 B1 | 10/2001 | Cheng et al. |
| 6,013,074 A | 1/2000 | Taylor | | 6,306,131 B1 | 10/2001 | Hareyama et al. |
| 6,014,581 A | 1/2000 | Whayne et al. | | 6,306,134 B1 | 10/2001 | Goble et al. |
| 6,017,338 A | 1/2000 | Brucker et al. | | 6,309,386 B1 | 10/2001 | Bek |
| 6,022,346 A | 2/2000 | Panescu et al. | | 6,322,558 B1 | 11/2001 | Taylor et al. |
| 6,022,347 A | 2/2000 | Lindenmeier et al. | | 6,325,799 B1 | 12/2001 | Goble |
| 6,033,399 A | 3/2000 | Gines | | 6,337,998 B1 | 1/2002 | Behl et al. |
| 6,039,731 A | 3/2000 | Taylor et al. | | 6,338,657 B1 | 1/2002 | Harper et al. |
| 6,039,732 A | 3/2000 | Ichikawa et al. | | 6,350,262 B1 | 2/2002 | Ashley |
| 6,041,260 A | 3/2000 | Stern et al. | | 6,358,245 B1 | 3/2002 | Edwards |
| 6,044,283 A | 3/2000 | Fein et al. | | 6,364,877 B1 | 4/2002 | Goble et al. |
| 6,053,910 A | 4/2000 | Fleenor | | 6,371,963 B1 | 4/2002 | Nishtala et al. |
| 6,053,912 A | 4/2000 | Panescu et al. | | 6,383,183 B1 | 5/2002 | Sekino et al. |
| 6,055,458 A | 4/2000 | Cochran et al. | | 6,391,024 B1 | 5/2002 | Sun et al. |
| 6,056,745 A | 5/2000 | Panescu et al. | | 6,398,779 B1 | 6/2002 | Buysse et al. |
| 6,056,746 A | 5/2000 | Goble et al. | | 6,398,781 B1 | 6/2002 | Goble et al. |
| 6,059,781 A | 5/2000 | Yamanashi et al. | | 6,402,741 B1 | 6/2002 | Keppel et al. |

| | | | | | | |
|---|---|---|---|---|---|---|
| 6,402,742 B1 | 6/2002 | Blewett et al. | | 6,696,844 B2 | 2/2004 | Taylor et al. |
| 6,402,743 B1 | 6/2002 | Orszulak et al. | | 6,712,813 B2 | 3/2004 | Ellman |
| 6,402,748 B1 | 6/2002 | Schoenman et al. | | 6,730,078 B2 | 5/2004 | Simpson et al. |
| 6,409,722 B1 | 6/2002 | Hoey et al. | | 6,730,079 B2 | 5/2004 | Lovewell |
| 6,413,256 B1 | 7/2002 | Truckai et al. | | 6,730,080 B2 | 5/2004 | Harano |
| 6,416,509 B1 | 7/2002 | Goble et al. | | 6,733,495 B1 | 5/2004 | Bek |
| 6,422,896 B2 | 7/2002 | Aoki et al. | | 6,733,498 B2 | 5/2004 | Paton |
| 6,423,057 B1 | 7/2002 | He et al. | | 6,740,079 B1 | 5/2004 | Eggers |
| 6,426,886 B1 | 7/2002 | Goder | | 6,740,085 B2 | 5/2004 | Hareyama |
| 6,428,537 B1 | 8/2002 | Swanson et al. | | 6,743,225 B2 | 6/2004 | Sanchez et al. |
| 6,436,096 B1 | 8/2002 | Hareyama | | 6,746,284 B1 | 6/2004 | Spink, Jr. |
| 6,440,157 B1 | 8/2002 | Shigezawa et al. | | 6,749,624 B2 | 6/2004 | Knowlton |
| 6,451,015 B1 | 9/2002 | Rittman, III et al. | | 6,755,825 B2 | 6/2004 | Shoenman et al. |
| 6,454,594 B2 | 9/2002 | Sawayanagi | | 6,758,846 B2 | 7/2004 | Goble et al. |
| 6,458,121 B1 | 10/2002 | Rosenstock | | 6,761,716 B2 | 7/2004 | Kadhiresan et al. |
| 6,458,122 B1 | 10/2002 | Pozzato | | 6,783,523 B2 | 8/2004 | Qin |
| 6,464,689 B1 | 10/2002 | Qin | | 6,784,405 B2 | 8/2004 | Flugstad et al. |
| 6,464,696 B1 | 10/2002 | Oyama | | 6,786,905 B2 | 9/2004 | Swanson et al. |
| 6,468,270 B1 | 10/2002 | Hovda et al. | | 6,790,206 B2 | 9/2004 | Panescu |
| 6,468,273 B1 | 10/2002 | Leveen et al. | | 6,792,390 B1 | 9/2004 | Burnside et al. |
| 6,482,201 B1 | 11/2002 | Olsen et al. | | 6,796,980 B2 | 9/2004 | Hall |
| 6,488,678 B2 | 12/2002 | Sherman | | 6,796,981 B2 | 9/2004 | Wham |
| 6,494,880 B1 | 12/2002 | Swanson et al. | | 6,809,508 B2 | 10/2004 | Donofrio |
| 6,497,659 B1 | 12/2002 | Rafert | | 6,818,000 B2 | 11/2004 | Muller et al. |
| 6,498,466 B1 | 12/2002 | Edwards | | 6,824,539 B2 | 11/2004 | Novak |
| 6,506,189 B1 | 1/2003 | Rittman, III et al. | | 6,830,569 B2 | 12/2004 | Thompson |
| 6,508,815 B1 | 1/2003 | Strul | | 6,837,888 B2 | 1/2005 | Ciarrocca et al. |
| 6,511,476 B2 | 1/2003 | Hareyama | | 6,843,682 B2 | 1/2005 | Matsuda et al. |
| 6,511,478 B1 | 1/2003 | Burnside | | 6,843,789 B2 | 1/2005 | Goble |
| 6,517,538 B1 | 2/2003 | Jacob et al. | | 6,849,073 B2 | 2/2005 | Hoey |
| 6,522,931 B2 | 2/2003 | Manker et al. | | 6,855,141 B2 | 2/2005 | Lovewell |
| 6,524,308 B1 | 2/2003 | Muller et al. | | 6,855,142 B2 | 2/2005 | Harano |
| 6,537,272 B2 | 3/2003 | Christopherson et al. | | 6,860,881 B2 | 3/2005 | Sturm |
| 6,544,260 B1 | 4/2003 | Markel et al. | | 6,864,686 B2 | 3/2005 | Novak |
| 6,546,270 B1 | 4/2003 | Goldin et al. | | 6,875,210 B2 | 4/2005 | Refior |
| 6,547,786 B1 | 4/2003 | Goble | | 6,890,331 B2 | 5/2005 | Kristensen |
| 6,557,559 B1 | 5/2003 | Eggers et al. | | 6,893,435 B2 | 5/2005 | Goble |
| 6,558,376 B2 | 5/2003 | Bishop | | 6,899,538 B2 | 5/2005 | Matoba |
| 6,558,377 B2 | 5/2003 | Lee et al. | | 6,923,804 B2 | 8/2005 | Eggers et al. |
| 6,560,470 B1 | 5/2003 | Pologe | | 6,929,641 B2 | 8/2005 | Goble et al. |
| 6,562,037 B2 | 5/2003 | Paton | | 6,936,047 B2 | 8/2005 | Nasab et al. |
| 6,565,559 B2 | 5/2003 | Eggleston | | 6,939,344 B2 | 9/2005 | Kreindel |
| 6,565,562 B1 | 5/2003 | Shah et al. | | 6,939,346 B2 | 9/2005 | Kannenberg et al. |
| 6,575,969 B1 | 6/2003 | Rittman, III et al. | | 6,939,347 B2 | 9/2005 | Thompson |
| 6,578,579 B2 | 6/2003 | Burnside et al. | | 6,942,660 B2 | 9/2005 | Pantera et al. |
| 6,579,288 B1 | 6/2003 | Swanson et al. | | 6,948,503 B2 | 9/2005 | Refior et al. |
| 6,582,427 B1 | 6/2003 | Goble et al. | | 6,958,064 B2 | 10/2005 | Rioux et al. |
| 6,602,243 B2 | 8/2003 | Noda | | 6,962,587 B2 | 11/2005 | Johnson et al. |
| 6,602,252 B2 | 8/2003 | Mollenauer | | 6,966,907 B2 | 11/2005 | Goble |
| 6,611,793 B1 | 8/2003 | Burnside et al. | | 6,974,453 B2 | 12/2005 | Woloszko et al. |
| 6,620,157 B1 * | 9/2003 | Dabney et al. ............. 606/34 | | 6,974,463 B2 | 12/2005 | Magers et al. |
| 6,620,189 B1 | 9/2003 | Machold et al. | | 6,977,495 B2 | 12/2005 | Donofrio |
| 6,623,423 B2 | 9/2003 | Sakurai et al. | | 6,984,231 B2 | 1/2006 | Goble |
| 6,626,901 B1 | 9/2003 | Treat et al. | | 6,989,010 B2 | 1/2006 | Francischelli et al. |
| 6,629,973 B1 | 10/2003 | Wardell et al. | | 6,994,704 B2 | 2/2006 | Qin et al. |
| 6,632,193 B1 | 10/2003 | Davison et al. | | 6,994,707 B2 | 2/2006 | Ellman et al. |
| 6,635,056 B2 | 10/2003 | Kadhiresan et al. | | 7,001,379 B2 | 2/2006 | Behl et al. |
| 6,635,057 B2 | 10/2003 | Harano | | 7,001,381 B2 | 2/2006 | Harano et al. |
| 6,645,198 B1 | 11/2003 | Bommannan et al. | | 7,004,174 B2 | 2/2006 | Eggers et al. |
| 6,648,883 B2 | 11/2003 | Francischelli | | 7,008,369 B2 | 3/2006 | Cuppen |
| 6,651,669 B1 | 11/2003 | Burnside | | 7,008,417 B2 | 3/2006 | Eick |
| 6,652,513 B2 | 11/2003 | Panescu et al. | | 7,008,421 B2 | 3/2006 | Daniel et al. |
| 6,652,514 B2 | 11/2003 | Ellman | | 7,025,764 B2 | 4/2006 | Paton et al. |
| 6,653,569 B1 | 11/2003 | Sung | | 7,033,351 B2 | 4/2006 | Howell |
| 6,656,177 B2 | 12/2003 | Truckai et al. | | 7,041,096 B2 | 5/2006 | Malis et al. |
| 6,663,623 B1 | 12/2003 | Oyama et al. | | 7,044,948 B2 | 5/2006 | Keppel |
| 6,663,624 B2 | 12/2003 | Edwards | | 7,044,949 B2 | 5/2006 | Orszulak et al. |
| 6,663,627 B2 | 12/2003 | Francischelli et al. | | 7,060,063 B2 | 6/2006 | Marion et al. |
| 6,666,860 B1 | 12/2003 | Takahashi | | 7,062,331 B2 | 6/2006 | Zarinetchi et al. |
| 6,672,151 B1 | 1/2004 | Schultz et al. | | 7,063,692 B2 | 6/2006 | Sakurai et al. |
| 6,679,875 B2 | 1/2004 | Honda | | 7,066,933 B2 | 6/2006 | Hagg |
| 6,682,527 B2 | 1/2004 | Strul | | 7,074,217 B2 | 7/2006 | Strul et al. |
| 6,685,700 B2 | 2/2004 | Behl | | 7,083,618 B2 | 8/2006 | Couture et al. |
| 6,685,701 B2 | 2/2004 | Orszulak et al. | | 7,094,231 B1 | 8/2006 | Ellman et al. |
| 6,685,703 B2 | 2/2004 | Pearson et al. | | RE39,358 E | 10/2006 | Goble |
| 6,689,131 B2 | 2/2004 | McClurken | | 7,115,121 B2 | 10/2006 | Novak |
| 6,692,489 B1 | 2/2004 | Heim | | 7,115,124 B1 | 10/2006 | Xiao |
| 6,693,782 B1 | 2/2004 | Lash | | 7,118,564 B2 | 10/2006 | Ritchie et al. |
| 6,695,837 B2 | 2/2004 | Howell | | 7,122,031 B2 | 10/2006 | Edwards et al. |

| Patent No. | Date | Inventor |
|---|---|---|
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 | 1/2003 | Wham et al. |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Flemming |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai |
| 2004/0024395 A1 | 2/2004 | Ellman |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm et al. |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0004634 A1 | 1/2005 | Ricart et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0109111 A1 | 5/2005 | Manlove et al. |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |

| | | | | | | |
|---|---|---|---|---|---|---|
| 2007/0225698 | A1 | 9/2007 | Orszulak et al. | EP | 1810633 | 7/2007 |
| 2007/0250052 | A1 | 10/2007 | Wham | EP | 1854423 | 11/2007 |
| 2007/0265612 | A1 | 11/2007 | Behnke et al. | FR | 1275415 | 10/1961 |
| 2007/0282320 | A1 | 12/2007 | Buysse et al. | FR | 1347865 | 11/1963 |
| 2008/0015563 | A1 | 1/2008 | Hoey et al. | FR | 2313708 | 12/1976 |
| 2008/0015564 | A1 | 1/2008 | Wham et al. | FR | 2364461 | 7/1978 |
| 2008/0039831 | A1 | 2/2008 | Odom et al. | FR | 2502935 | 10/1982 |
| 2008/0039836 | A1 | 2/2008 | Odom et al. | FR | 2517953 | 6/1983 |
| 2008/0082094 | A1 | 4/2008 | McPherson et al. | FR | 2573301 | 5/1986 |
| 2008/0125767 | A1 | 5/2008 | Blaha | GB | 607850 | 9/1948 |
| 2008/0177199 | A1 | 7/2008 | Podhajsky | GB | 702510 | 1/1954 |
| 2008/0248685 | A1 | 10/2008 | Sartor et al. | GB | 855459 | 11/1960 |
| 2008/0281315 | A1 | 11/2008 | Gines | GB | 902775 | 8/1962 |
| 2008/0281316 | A1 | 11/2008 | Carlton et al. | GB | 2164473 | 3/1986 |
| 2008/0287791 | A1 | 11/2008 | Orszulak et al. | GB | 2214430 | 9/1989 |
| 2008/0287838 | A1 | 11/2008 | Orszulak et al. | GB | 2358934 | 8/2001 |
| 2009/0018536 | A1 | 1/2009 | Behnke | SU | 166452 | 1/1965 |
| 2009/0024120 | A1 | 1/2009 | Sartor | SU | 727201 | 4/1980 |
| 2009/0036883 | A1 | 2/2009 | Behnke | WO | WO92/06642 | 4/1992 |
| 2009/0069801 | A1 | 3/2009 | Jensen et al. | WO | WO93/24066 | 12/1993 |
| 2009/0082765 | A1 | 3/2009 | Collins et al. | WO | WO94/24949 | 11/1994 |
| 2009/0157071 | A1 | 6/2009 | Wham et al. | WO | WO94/28809 | 12/1994 |
| 2009/0157072 | A1 | 6/2009 | Wham et al. | WO | WO95/09577 | 4/1995 |
| 2009/0157073 | A1 | 6/2009 | Orszulak | WO | WO95/19148 | 7/1995 |
| 2009/0157075 | A1 | 6/2009 | Wham et al. | WO | WO95/25471 | 9/1995 |

FOREIGN PATENT DOCUMENTS

| | | | | | |
|---|---|---|---|---|---|
| DE | 1099658 | 2/1961 | WO | WO96/02180 | 2/1996 |
| DE | 1139927 | 11/1962 | WO | WO96/04860 | 2/1996 |
| DE | 1149832 | 6/1963 | WO | WO96/08794 | 3/1996 |
| DE | 1439302 | 1/1969 | WO | WO96/18349 | 6/1996 |
| DE | 2439587 | 2/1975 | WO | WO96/29946 | 10/1996 |
| DE | 2455174 | 5/1975 | WO | WO96/39086 | 12/1996 |
| DE | 2407559 | 8/1975 | WO | WO96/39914 | 12/1996 |
| DE | 2602517 | 7/1976 | WO | WO97/06739 | 2/1997 |
| DE | 2504280 | 8/1976 | WO | WO97/06740 | 2/1997 |
| DE | 2540968 | 3/1977 | WO | WO97/06855 | 2/1997 |
| DE | 2820908 | 11/1978 | WO | WO97/11648 | 4/1997 |
| DE | 2803275 | 8/1979 | WO | WO97/17029 | 5/1997 |
| DE | 2823291 | 11/1979 | WO | WO98/07378 | 2/1998 |
| DE | 2946728 | 5/1981 | WO | WO98/18395 | 5/1998 |
| DE | 3143421 | 5/1982 | WO | WO98/27880 | 7/1998 |
| DE | 3045996 | 7/1982 | WO | WO99/12607 | 3/1999 |
| DE | 3120102 | 12/1982 | WO | WO02/00129 | 1/2002 |
| DE | 3510586 | 10/1986 | WO | WO02/11634 | 2/2002 |
| DE | 3604823 | 8/1987 | WO | WO02/45589 | 6/2002 |
| DE | 390937 | 4/1989 | WO | WO02/47565 | 6/2002 |
| DE | 3904558 | 8/1990 | WO | WO02/053048 | 7/2002 |
| DE | 3942998 | 7/1991 | WO | WO02/088128 | 7/2002 |
| DE | 4339049 | 5/1995 | WO | WO03/090630 | 11/2003 |
| DE | 19717411 | 11/1998 | WO | WO03/090635 | * 11/2003 |
| DE | 19848540 | 5/2000 | WO | WO03/092520 | 11/2003 |
| EP | 246350 | 11/1987 | WO | WO2005/060365 | 11/2003 |
| EP | 310431 | 4/1989 | WO | WO2004/028385 | 4/2004 |
| EP | 325456 | 7/1989 | WO | WO2004/098385 | 4/2004 |
| EP | 336742 | 10/1989 | WO | WO2004/043240 | 5/2004 |
| EP | 390937 | 10/1990 | WO | WO2004/052182 | 6/2004 |
| EP | 556705 | 8/1993 | WO | WO2004/103156 | 12/2004 |
| EP | 569130 | 11/1993 | WO | WO2005/046496 | 5/2005 |
| EP | 608609 | 8/1994 | WO | WO2005/048809 | 6/2005 |
| EP | 0694291 | * 1/1996 | WO | WO2005/050151 | 6/2005 |
| EP | 836868 | 4/1998 | WO | WO2005/060849 | * 7/2005 |
| EP | 878169 | 11/1998 | WO | WO2006/050888 | 5/2006 |
| EP | 1051948 | * 11/2000 | WO | WO2006/105121 | 10/2006 |
| EP | 1053720 | 11/2000 | | | |
| EP | 1151725 | 11/2001 | | | |
| EP | 1293171 | 3/2003 | | | |
| EP | 1472984 | 11/2004 | | | |
| EP | 1495712 | * 1/2005 | | | |
| EP | 1500378 | * 1/2005 | | | |
| EP | 1535581 | * 6/2005 | | | |
| EP | 1609430 | 12/2005 | | | |
| EP | 1707144 | 3/2006 | | | |
| EP | 1645235 | 4/2006 | | | |
| EP | 880220 | 6/2006 | | | |
| EP | 1707143 | * 10/2006 | | | |
| EP | 1744354 | 1/2007 | | | |
| EP | 1 810630 | 7/2007 | | | |
| EP | 1810628 | 7/2007 | | | |

OTHER PUBLICATIONS

International Search Report EP 07010673.7; dated Sep. 24, 2007.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic Computerized Bipolar Coagulator" Journal of Neurosurgery 75:1, (Jul. 1991) pp. 148-151.

Chicharo et al. "A Sliding Goertzel Algorith" Aug. 1996, pp. 283-297 Signal Processing, Elsevier Science Publishers B.V. Amsterdam, NL vol. 52 No. 3.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedence" Am. J. MI, Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure "The O.R. Pro 300" 1 p. Sep. 1998.

Ogden Goertzel Alternative to the Fourier Transform: Jun. 1993 pp. 485-487 Electronics World; Reed Business Publishing, Sutton, Surrey, BG vol. 99, No. 9. 1687.

Sugita et al., "Bipolar Coagulator with Automatic Thermocontrol" J. Neurosurg., vol. 41, Dec. 1944, pp. 777-779.

Valleylab Brochure "Valleylab Electroshield Monitoring System" 2 pp. Nov. 1995.

Vallfors et al., "Automatically Controlled Bipolar Electrosoagulation-'COA-COMP'" Neurosurgical Review 7:2-3 (1984) pp. 187-190.

Wald et al., "Accidental Burns", JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp. Jan. 1989.

Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.

International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP09158915 dated Jul. 14, 2009.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP06022028.2 dated Feb. 5, 2007.*
International Search Report EP06025700.3. dated Apr. 12, 2007.*
International Search Report EP07001481.6 dated Apr. 23, 2007.*
International Search Report EP07001485.7 dated May 15, 2007.*
International Search Report EP07001527.6 dated May 9, 2007.*
International Search Report EP07004355.9 dated May 21, 2007.*
Muller et al., "Extended Left Hemicolectomy Using the LigaSure Vessel Sealing System" Innovations That Work; Sep. 1999.*
European Examination Report issued in counterpart EP Application No. EP09158915.0 dated Apr. 1, 2010.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
US 6,878,148, 04/2005, Goble et al. (withdrawn)

* cited by examiner

SYSTEM AND METHOD FOR CLOSED LOOP MONITORING OF MONOPOLAR ELECTROSURGICAL APPARATUS

PRIORITY CLAIM

This application claims priority to a U.S. Provisional Application Ser. No. 60/761,440 entitled "System and Method for Closed Loop Monitoring of Monopolar Electrosurgical Apparatus" filed by Robert Wham et al. on Jan. 24, 2006. The entire contents of which is incorporated by reference herein.

BACKGROUND

1. Field

The present disclosure relates generally to electrosurgical system and method, more specifically, to a system and method for closed loop monitoring of monopolar electrosurgical apparatus to sense tissue and energy properties and control energy delivery based on the sensed properties.

2. Description of the Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active (current supplying) electrode such that an electrical circuit is formed between the two electrodes. Commonly, electrodes in bipolar electrosurgical systems are disposed within electrosurgical forceps, which lend itself particularly well to vessel sealing. In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Electrosurgical generators are capable of producing a variety of electrical waveforms. Certain waveforms are better suited for specific electrosurgical procedures. A continuous waveform having a duty cycle of 100% is best suited for cutting the tissue since the energy produces heat very rapidly thereby vaporizing the tissue. An intermittent waveform, where the duty cycle of about 10% is best suited for coagulating the tissue since the amount of heat generated is reduced.

Currently parameters affecting the coagulation waveform are adjusted manually by the surgeon. This adjustment process is cumbersome since the coagulation waveform may need to be adjusted continuously during its delivery. However, there are no systems available which can adjust the coagulation waveform automatically.

SUMMARY

The present disclosure provides for an electrosurgical system having closed loop monitoring. The system includes an electrosurgical generator having an RF output stage for generating electrosurgical waveforms suitable for coagulation and a microprocessor for controlling the RF output stage. The closed loop monitoring includes a sensor for sensing one or more tissue properties, such as voltage, current, temperature. The sensor transmits data pertaining to the tissue properties to the microprocessor which adjusts generator output. More specifically, the generator adjusts the electrosurgical waveforms in response to the data to correspond with predetermined waveform parameters.

An electrosurgical system is also disclosed, which is configured to provide automatic closed loop control of the RF energy in direct response to tissue changes until a desired clinical hemostasis effect is achieved. The system includes a generator having a high speed high voltage power source ("HVPS") for supplying direct current ("DC") output. The HVPS is configured to adjust DC output in a rapid and dynamic fashion. The generator includes an RF output stage which is configured to generate radio frequency ("RF") energy comprising one or more electrosurgical coagulation waveforms suitable for coagulating tissue. The system also includes an RF sensor for sensing properties of the RF energy and generating an RF signal indicative of the RF energy. The sampling rates for sensing are sufficient to allow the generator to sculpt the electrosurgical coagulation waveforms in real time as a function of the RF sensor signal in order to match the waveforms to the RF stage. The system further includes a closed loop control system which controls the electrosurgical coagulation waveform. Additionally, the system includes one or more gain controllers configured to amplify the RF sensor signal to maintain a predetermined signal to noise ratio and to provide RF voltage and current correction of the RF sensor signal which is then transmitted to the controller to allow for real time modification of RF energy.

According to one aspect of the present disclosure an electrosurgical system is disclosed which includes a generator configured to generate electrosurgical coagulation waveforms. The generator includes a closed loop control system which controls the electrosurgical coagulation waveforms. The closed loop control system includes a sensor configured to sense a tissue property or an energy property and transmit the tissue property or an energy property as one or more sensor signals having an amplitude. The control system also includes a gain controller configured to process the sensor signals to reduce the amplitude thereof and to obtain a signal to noise ratio of the sensor signals within a predetermine range. Microprocessor is coupled to the generator and is configured to adjust the electrosurgical coagulation waveforms as a function of the sensor signals.

According to another aspect of the present disclosure a closed loop control system for controlling electrosurgical coagulation waveforms is disclosed. The closed loop control system includes a sensor configured to sense a tissue property or an energy property and transmit the tissue property or energy property as one or more sensor signals having an amplitude. The control system also includes a gain controller configured to process the sensor signals to reduce the amplitude thereof and to obtain a signal to noise ratio of the sensor signals within a predetermine range. Microprocessor is coupled to the generator and is configured to adjust the electrosurgical coagulation waveforms as a function of the sensor signals.

A method for controlling electrosurgical coagulation waveforms is also contemplated by the present disclosure. The method includes the steps of sensing a tissue property or an energy property and transmitting the tissue property or an energy property as sensor signals having an amplitude and processing the sensor signals to reduce the amplitude thereof and to obtain a signal to noise ratio of the sensor signals within a predetermine range. The method also includes the step of adjusting the electrosurgical coagulation waveforms as a function of the sensor signals.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

The present disclosure provides for an electrosurgical system having precision closed loop monitoring of tissue and energy properties. The system includes a generator which is configured for high-speed power sourcing of radio frequency (RF) energy. The control loop includes a plurality of sensors for sensing tissue and energy properties and gain control for modifying generator output. The sensors monitor tissue properties in real time to allow an embedded controller to provide corrective adjustment to the delivered RF energy. The closed control loop automatically corrects the applied RF energy, based on tissue and energy properties according to prescribed algorithm determined by the clinical procedure. The generator receives the corrective adjustment from the controller and dynamically modifies the delivered energy in direct response to changes in tissue properties until a desired clinical effect is achieved.

Figure 1:
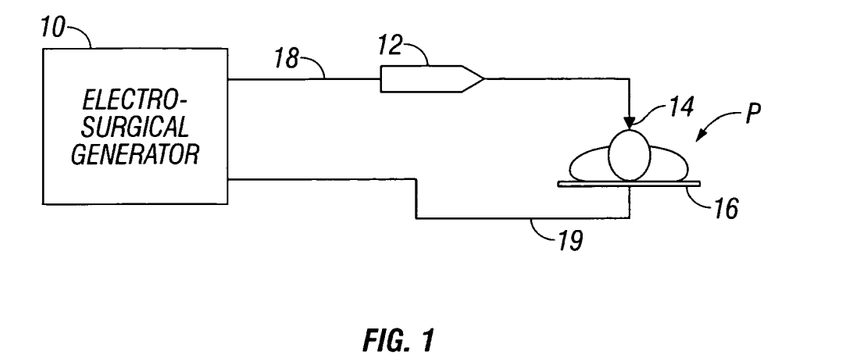
FIG. 1 is a schematic block diagram of an electrosurgical system.

FIG. 1 is a schematic illustration of an electrosurgical system 1 configured for a monopolar procedure. The system 1 includes an active electrode 14 and a return electrode 16 for treating tissue of a patient P. Electrosurgical RF energy is supplied to the active electrode 14 by a generator 10 via a cable 18 allowing the active electrode 14 to ablate, cut or coagulate the tissue. The return electrode 16 is placed at the patient P to return the energy from the patient P to the generator 10 via a cable 19.

The generator 10 includes input controls (e.g., buttons, activators, switches, etc.) for controlling the generator 10. The controls allow the surgeon to adjust power of the RF energy, waveform, and other parameters to achieve the desired waveform suitable for a particular task (e.g., cutting, coagulating, etc.). Disposed between the generator 10 and the active electrode 14 on the cable 18 is a hand piece 12, which includes a plurality of input controls which may be redundant with certain input controls of the generator 10. Placing the input controls at the hand piece 12 allows for easier and faster modification of RF energy parameters during the surgical procedure without returning to the generator 10. It is also envisioned that a footswitch may be connected to the generator 10 to control energy delivery during monopolar procedures. It is further envisioned that the hand piece 12 and the electrode 14 can be incorporated into a single instrument e.g., a surgical pencil, with the electrode 14 being disposed at a distal end of the hand piece 12.

Figure 2:
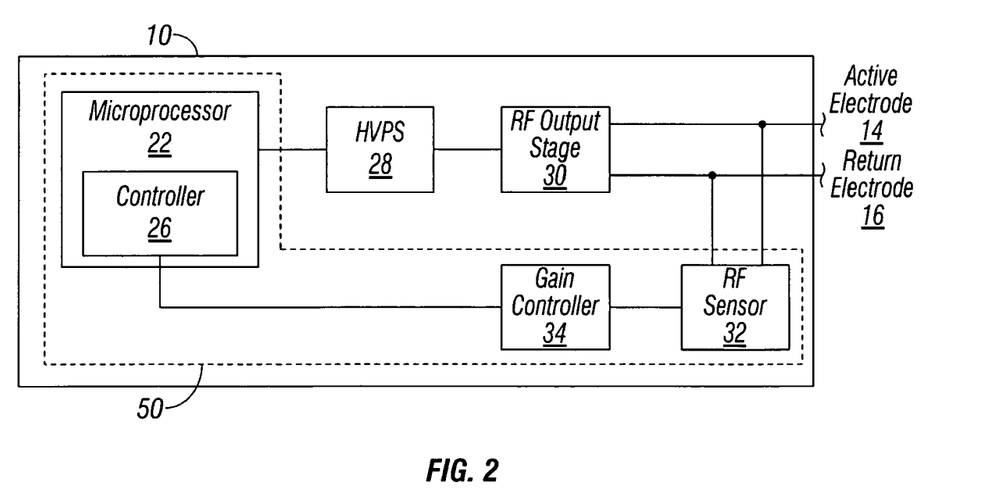
FIG. 2 is a schematic block diagram of a generator according to the present disclosure.

FIG. 2 shows a schematic block diagram of the generator 10 having a microprocessor 22, a high speed high voltage power source ("HVPS") 28 for supplying direct current ("DC") output, an RF output stage 30, at least one RF sensor 32 configured to measure one or more tissue and/or energy properties, and a gain controller 34. The microprocessor 22 includes a controller 26 and an output port which is electrically connected to the HVPS 28 configured to supply DC voltage, from about 0 V to about 200 V, to the RF output stage 30. The microprocessor 22 receives input signals from the generator 10, the hand piece 12, or the footswitch and the controller 26, in turn, adjusts output parameters of the generator 10, more specifically the HVPS 28, and/or performs other control functions thereon. It is also envisioned that the controller 26 is configured to receive control signals from the gain controller 34 for dynamic adjustment to the RF energy being delivered to the tissue.

The RF output stage 30 converts DC power into RF energy and delivers the RF energy, at about 470 KHz, to the active electrode 14 or other electrosurgical devices connected to the generator 10. In addition, the RF output stage 30 also receives RF energy from the return electrode 16. The RF sensor 32 is connected to the input and output (e.g., the connections to the active electrode 14 and the return electrode 16) of the RF output stage 30 to sense tissue and energy properties (e.g., impedance, voltage, current, temperature, phase, voltage peak, crest factor, current peak, real and reactive power, voltage rate change over time [dv/dt], phase rate change over time [dφ/dt], current rate change over time [dI/dt], temperature rate change over time [dT/dt], impedance rate change over time [dz/dt], high order harmonics of the fundamental 472 kHz waveform, etc.)

The generator 10 includes a closed loop control system 50 having the microprocessor 22, the controller 26, the RF sensor 32 and the gain controller 34 along with components thereof shown in FIGS. 3A-B and discussed in more detail below. The RF sensor 32 transmits signals representing tissue and/or energy properties through the gain control 34 to adjust the RF energy output accordingly. Sensed properties are transmitted to the microprocessor 22 and the controller 26 to perform calculations to determine the adjustments which have to be made to the RF energy output. The microprocessor 22 compares impedance, voltage, and other measurements to desired values and signals the RF output stage 30 to make any adjustments necessary to achieve the desired values.

In addition to impedance and voltage, the microprocessor 22 also measures voltage at a peak of the waveform (Vpk) and root-mean-square voltage (Vrms). Peak and rms calculations are also performed using current (I) value. To calculate rms values, the sample rates of the voltage and current signals must correspond to the buffer size of the sensor 32. More specifically, the microprocessor 22 includes a buffer which is sized so that it contains an integer number of full cycles of the waveform at a specified sample rate to avoid modulation errors within the rms values. This allows the sensor 32 to tailor the data acquisition to the varied waveforms associated with coagulation RF energy.

The microprocessor 22 calculates crest factor (Vpk/Vrms or Ipk/Irms) and V and I peak values in real time and controls output waveform timing and RF amplitude as a function thereof. It is envisioned that real time calculation of crest factor can be used to adjust the RF energy or adjust the waveform to keep a crest factor profile. More specifically, real time calculation of crest factor allows for coagulation modes to be controlled by adjusting the output RF energy to maintain a predetermined crest factor. Either crest factor or V and I peak values can be held constant and adjust the output waveform timing and RF amplitude accordingly.

The gain controller 34 processes sensed voltage and current signals received from the RF sensor 32. More specifically, the gain controller 34 reduces high amplitudes of coagulation voltage and current signals which allows for the signals to be transmitted into the microprocessor 22 for processing. The gain control 34 provides for both amplification and attenuation of the voltage and current signals to obtain good signal to noise ratios to minimize bit quantization error. Resolution and accuracy of the sensed RF delivered to precisely control the patient energy dosage.

Figure 3A:
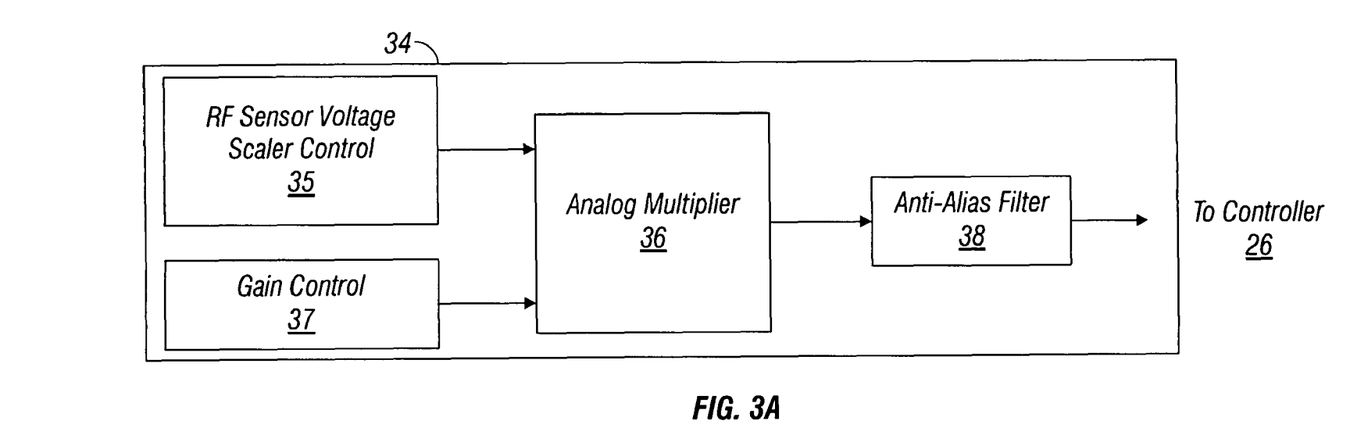
FIGS. 3A-B are a schematic block diagrams of closed loop coagulation control according to the present disclosure.
Figure 3B:
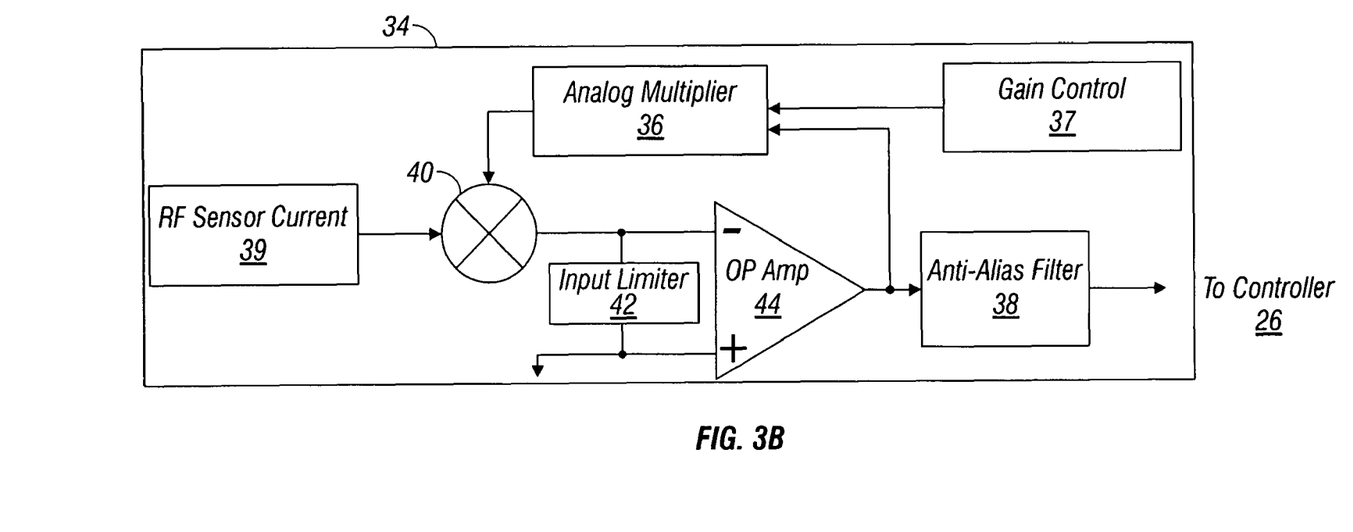

With reference to FIGS. 3A-B, the gain control process is illustrated in two embodiments. FIG. 3A, shows the gain controller 34 which includes RF sensor voltage scaler control 35 and a gain control 37 connected to an analog multiplier 36 which is then connected to an anti-alias filter 38. In this embodiment, the gain controller 34 adjusts the sensed voltage of the RF energy. The voltage scaler 35 which receives RF signals (e.g., signals representative of the RF energy being outputted by the generator 10) from the RF sensor 32 and dynamically and automatically scales the RF signal to adjust the high amplitude levels of the RF coagulation voltage and current signals. The gain control 37 provides real time gain modification of the RF energy by processing a variable DC level control signal received from the controller 26. The analog multiplier 36 performs a real time multiplication of signal inputs received from the outputs of the voltage scaler 35 and the gain control 37. The analog multiplier 36 normalizes the RF sensor signals independent of the high amplitude levels of the RF output 30 to maximize the precision of the delivered RF energy.

The anti-alias filter 38 blocks the RF frequency harmonics from contributing errors to the computed processing performed by the controller 26. The filter 38 processes the RF energy to reduce RF noise components and increase the accuracy of the delivered RF energy to the patient. It is also envisioned that the RF sensor 32 also includes an amplitude reduction circuit (not shown) to protect the front end of the multiplier 44.

FIG. 3B shows another embodiment of the gain controller 34 which includes an RF sensor current scaler control 39. In this embodiment, the gain controller 34 adjusts the sensed current of the RF energy. Gain control 37 is connected to the analog multiplier 36 and anti-alias components in similar manner as shown in FIG. 3A and discussed above. The output from the anti-alias filter 38 is fed to the output line (e.g., leading to the controller 26). In FIG. 3B, the output of the analog multiplier 36 is current mapped 1:1 to the RF sensor current input received from the RF sensor 32. Summer 40 processes the difference signals between the analog multiplier 36 and the RF sensor current input in conjunction with an operational amplifier ("OP amp") 44 to create an equivalent normalized RF output signal independent of the high amplitude levels of the RF output stage 30. Input limiter 42 provides surge protection to the OP amp 44 input, to increase the reliability of the gain controller 34.

The generator 10 is capable of making small adjustments to the RF waveform of high resolution (e.g., 10 ns). This allows control of crest factor and peak outputs as well as tuning of the output waveforms so that the output frequency can be adjusted to match the resonant frequency of the RF output stage 30. The generator 10 is configured to sculpt output curves to a degree using a linear interpolation method which allows any curve described within a predetermined number of points (e.g., 15), where the curves represent either current, power, voltage etc.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical system comprising:
   a generator configured to generate at least one electrosurgical coagulation waveform, the generator includes a closed loop control system that controls the at least one electrosurgical coagulation waveform, the closed loop control system including:
   a sensor configured to sense at least one of a tissue property and an energy property and transmit the at least one of a tissue property and an energy property to a gain controller as a voltage sensor signal having an amplitude;
   the gain controller configured to process the voltage sensor signal to reduce the amplitude of the voltage sensor signal and obtain a signal to noise ratio of the voltage sensor signal within a predetermine range;
   the gain controller being a voltage gain controller that includes:
      a sensor voltage scaler control configured to scale the amplitude of the voltage sensor signal and to generate a scaled sensor signal;
      a gain control configured to process a variable DC level control signal to generate a gain control signal; and
      a multiplier coupled to the sensor voltage scaler and the gain control, the multiplier configured to multiply in real-time the scaled sensor signal and the gain control signal to normalize the voltage sensor signal independent of the amplitude thereof; and
   a microprocessor coupled to the generator and configured to adjust the at least one electrosurgical coagulation waveform as a function of the voltage sensor signal.

2. An electrosurgical system according to claim 1, wherein the voltage gain controller includes:
   an anti-alias filter configured to substantially block a harmonic radio frequency.

3. An electrosurgical system according to claim 1, wherein the microprocessor includes a buffer sized to store an integer multiple of a repetition rate of the voltage sensor signal.

4. An electrosurgical system according to claim 1, wherein the microprocessor is configured to calculate at least one of a RMS value, a peak value, and crest factor of the voltage sensor signal and adjust the at least one electrosurgical coagulation waveform as a function thereof.

5. An electrosurgical system comprising:
   a generator configured to generate at least one electrosurgical coagulation waveform, the generator includes a closed loop control system which controls the at least one electrosurgical coagulation waveform, the closed loop control system including:
   a sensor configured to sense at least one of a tissue property and an energy property and transmit the at least one of a tissue property and an energy property to a gain controller as a current sensor signal having an amplitude;
   the gain controller configured to process the current sensor signal to reduce the amplitude of the current sensor signal and obtain a signal to noise ratio of the current sensor signal within a predetermine range;
   the gain controller being a current gain controller that includes:

a sensor current scaler control configured to scale the amplitude of the current sensor signal and to generate a scaled sensor signal;
a gain control configured to process a variable DC level control signal to generate a gain control signal;
a multiplier configured to generate a multiplied signal as a function of the real-time the gain control signal;
a summer configured to generate a difference signal as a function of the multiplied signal and the current sensor signal; and
an operational amplifier configured to amplify the difference signal to normalize the current sensor signal independent of the amplitude thereof; and
a microprocessor coupled to the generator and configured to adjust the at least one electrosurgical coagulation waveform as a function of the current sensor signal.

6. An electrosurgical system according to claim 5, wherein the current gain controller includes:
an input limiter to provide surge protection for the operational amplifier.

7. An electrosurgical system according to claim 5, wherein the current gain controller includes:
an anti-alias filter configured to substantially block a harmonic radio frequency.

8. An electrosurgical system according to claim 5, wherein the microprocessor includes a buffer sized to store an integer multiple of a repetition rate of the current sensor signal.

9. An electrosurgical system according to claim 5, wherein the microprocessor is configured to calculate at least one of a RMS value, a peak value, and crest factor of the current sensor signal and adjust the at least one electrosurgical coagulation waveform as a function thereof.

10. A closed loop control system for controlling at least one electrosurgical coagulation waveform, the closed loop control system including:
a sensor configured to sense at least one of a tissue property and an energy property and transmit the at least one of a tissue property and an energy property to a gain controller as a voltage sensor signal having an amplitude;
the gain controller configured to process the voltage sensor signal to reduce the amplitude of the sensor signal and to obtain a signal to noise ratio of the voltage sensor signal within a predetermine range;
the gain controller being a voltage gain controller that includes:
a sensor voltage scaler control configured to scale the amplitude of the voltage sensor signal and to generate a scaled sensor signal;
a gain control configured to process a variable DC level control signal to generate a gain control signal; and
a multiplier coupled to the sensor voltage scaler and the gain control, the multiplier configured to multiply in real-time the scaled sensor signal and the gain control signal to normalize the voltage sensor signal independent of the amplitude thereof; and
a microprocessor coupled to the generator configured to adjust the at least one electrosurgical coagulation waveform as a function of the voltage sensor signal.

11. A closed loop control system according to claim 10, wherein the voltage gain controller includes:
an anti-alias filter configured to substantially block a harmonic radio frequency.

12. A closed loop control system for controlling at least one electrosurgical coagulation waveform, the closed loop control system including:
a sensor configured to sense at least one of a tissue property and an energy property and transmit the at least one of a tissue property and an energy property to a gain controller as a current sensor signal having an amplitude;
the gain controller configured to process the sensor signal to reduce the amplitude of the current sensor signal and to obtain a signal to noise ratio of the current sensor signal within a predetermine range;
the gain controller being a current gain controller that includes:
a sensor current scaler control configured to scale the amplitude of the current sensor signal and to generate a scaled sensor signal;
a gain control configured to process a variable DC level control signal to generate a gain control signal;
a multiplier configured to generate a multiplied signal as a function of the real-time the gain control signal;
a summer configured to generate a difference signal as a function of the multiplied signal and the current sensor signal; and
an operational amplifier configured to amplify the difference signal to normalize the current sensor signal independent of the amplitude thereof; and
a microprocessor coupled to the generator configured to adjust the at least one electrosurgical coagulation waveform as a function of the current sensor signal.

13. A closed loop control system according to claim 12, wherein the current gain controller includes:
an input limiter to provide surge protection for operational amplifier.

14. An electrosurgical system according to claim 12, wherein the current gain controller includes:
an anti-alias filter configured to substantially block a harmonic radio frequency.

15. A method for controlling at least one electrosurgical coagulation waveform, the closed loop control system including:
sensing at least one of a tissue property and an energy property and transmitting the at least one of a tissue property and an energy property as a sensor signal having an amplitude;
processing the sensor signal to reduce the amplitude of the sensor signal and to obtain a signal to noise ratio of the sensor signal within a predetermine range; and
adjusting the at least one electrosurgical coagulation waveform as a function of the sensor signal.

16. A method according to claim 15, further comprising the steps of:
scaling the amplitude of the sensor signal to generate a scaled sensor signal;
processing a variable DC level control signal to generate a gain control signal; and
multiplying in real-time the sealed sensor signal and the gain control signal to normalize the sensor signal independent of the amplitude thereof.

17. A method according to claim 16, further comprising the steps of
generating a difference signal as a function of the multiplied signal and the current sensor signal; and
amplifying the difference signal to normalize the current sensor signal independent of the amplitude thereof.

18. A method according to claim 15, further comprising the step of:
calculating one of a RMS value, a peak value, and crest factor of the sensor signal and adjusting the at least one electrosurgical coagulation waveform as a function thereof.

* * * * *